United States Patent [19]

Kamada

[11] Patent Number: 5,738,848
[45] Date of Patent: Apr. 14, 1998

[54] IMMUNOSUPPRESSIVE COMPOUNDS AND METHOD OF PREPARING SAME

[76] Inventor: Naoshi Kamada, 13 Stawell Place, Middle Park, Queensland 4074, Australia

[21] Appl. No.: 696,991

[22] PCT Filed: Feb. 16, 1995

[86] PCT No.: PCT/AU95/00072

§ 371 Date: Aug. 14, 1996

§ 102(e) Date: Aug. 14, 1996

[87] PCT Pub. No.: WO95/22559

PCT Pub. Date: Aug. 24, 1995

[30] Foreign Application Priority Data

Feb. 16, 1994 [AU] Australia ............................... PM3918
Feb. 16, 1994 [AU] Australia ............................... PM3919
Feb. 16, 1994 [AU] Australia ............................... PM3920

[51] Int. Cl.$^6$ .......................... A61K 38/17; A61K 38/02; C07K 2/00
[52] U.S. Cl. ..................... 424/185.1; 424/278.1; 514/2; 514/21; 530/412; 530/380
[58] Field of Search ............ 514/2, 21; 424/185.1; 530/413, 412, 380

[56] References Cited

FOREIGN PATENT DOCUMENTS

18417/88  1/1989  Australia .
WO 94/06449  3/1994  WIPO .

OTHER PUBLICATIONS

Burnham, NL. Am J Hosp Pharm. 51:210–218, Jan. 15, 1994.

Macy, E et al. J Allergy Clin Immunol. 83(5):871–875, May 1989.

J. Biochem vol. 107 No. 3 (1990), Shinomiya, T., et al. "Rat Liver Arginase Suppresses Mixed Lymphocyte Reaction", pp. 435–439.

Kiev Urology Institute, "Liver Allo–Transplant Detachment Prevention by Immunodepressant Therapy and Additional Proteinase Inhibitor" Derwent Abstract Accession No. 91–206472/28, Class B05, SU 1588420–A, 30 Aug. 1990 (Abstract Only).

Primary Examiner—David Saunders
Assistant Examiner—F. Pierre VanderVegt
Attorney, Agent, or Firm—Panitch Schwarze Jacobs & Nadel, P.C.

[57] ABSTRACT

The present invention relates to compounds which have immunosuppressive effects in mammals. In particular, the invention provides a protein which suppresses allograph rejection in a mammalian receipient. The protein is found in serum of a post liver transplantation subject and has a molecular weight selected from a molecular weight of about 10 kD, about 40 kD or about 87 kD, or is a homologue of a 10 kD, 40 kD or 87 kD protein found in serum of a post liver transplantation rat. The invention also provides a method of identifying immunosuppressive proteins, a process for preparing immunosuppressive proteins, compositions comprising immunosuppressive proteins and a method of suppressing allograft rejection in a mammalian recipient of a graft.

12 Claims, 2 Drawing Sheets

IMMUNOSUPPRESSIVE COMPOUNDS AND METHOD OF PREPARING SAME

This application is a 371 of PCT/AU95/00072.

TECHNICAL FIELD

This invention is directed to compounds which prevent rejection of transplanted tissue in a mammal, a method of isolating the compounds and a method of preventing rejection of transplanted tissue in a mammal.

BACKGROUND ART

Organ transplants, particularly kidney transplants, have become routine surgical procedures. However, transplants of organs such as heart, lung, pancreas or lower bowel are infrequently performed because of rejection of the transplanted organ by the recipient's immune system. Rejection is similarly a problem with kidney transplants.

An essential pre-requisite to transplantation is the screening of potential donors for identity of the donor histocompatibility complex with that of the recipient. However, with the exception of monozygotic twins, finding a donor with an identical histocompatibility complex is virtually impossible. Reliance must therefore be had on immunosuppressants so that the transplanted organ will not be rejected by the recipient's immune system.

Immunosuppressive compounds suitable for use in conjunction with organ transplantation include purine analogs such as 6-mercaptopurine, corticosteroids such as prednisone and prednisolone, antilymphocyte globulin, certain antibiotics such as cyclosporin A, and monoclonal antibodies specific for the IL-2 receptor. All of the above compounds have the disadvantage that they have general immunosuppressive effects. Hence, all tissues are damaged where rapid cell division is occurring.

Known immunosuppressive compounds also have undesirable side effects. This is particularly the case with the most widely used immunosuppressant cyclosporin A. Transplant recipients on cyclosporin A therapy invariably develop a cancer within 30 years of commencing therapy.

Another major drawback of immunosuppression with compounds such as cyclosporin A is the cost of therapy. Immunosuppression therapy with existing immunosuppressants must be maintained throughout the life of a transplant recipient. Cyclosporin A therapy currently costs about $1,000 per month per patient.

There is thus a pressing need for a compound which can be used to suppress rejection of a transplanted organ in a recipient but which does not have the disadvantages of the immunosuppressants currently used in conjunction with organ transplantation. Desirable properties of such a compound can be specified as follows: (i) relative specificity as an inhibitor of organ rejection but limited activity as a general immunosuppressant, (ii) an absence of undesirable side effects such as cell toxicity or carcinogenicity; and (iii) a relatively low cost or a biological activity which obviates long term therapy with the compound.

SUMMARY OF THE INVENTION

It is an object of this invention to provide compounds which suppress allograft rejection in a mammalian recipient and overcome the disadvantages of compounds presently used to prevent rejection of transplanted organs.

Further objects of the invention are to provide a method of identifying compounds which suppress allograft rejection in a mammalian subject, a method of isolating such compounds, and a method of suppressing allograft rejection.

In one aspect, the invention provides a protein which suppresses allograft rejection in a mammalian recipient, which protein is found in serum of a post liver transplantation subject and has a molecular weight selected from a molecular weight of about 10 kD, about 40 kD or about 87 kD, or is a homologue of a 10 kD, 40 kD or 87 kD protein found in serum of a post liver transplantation rat.

A preferred protein is a protein found in serum of a post orthotopic liver transplantation or re-transplantation rat which has the following N-terminal amino acid sequence:

| | |
|---|---|
| V H G A D A E T A I V N G X I | (SEQ ID NO:1) |
| X S L A A T H M H G N | (SEQ ID NO:2) |
| X E D I N F Q A F V E P H V | (SEQ ID NO:3) |

In another aspect, the invention provides a method of identifying immunosuppressive proteins, the method comprising the steps of:

i) obtaining a serum sample from a subject after liver transplantation;

ii) subjecting the serum sample to a separative technique;

iii) comparing separated proteins in the serum sample from (i) with separated proteins in a serum sample from a normal subject; and iv) identifying proteins which appear in serum in response to liver transplantation.

In yet another aspect, the invention provides a process for preparing a protein which suppresses allograft rejection in a mammalian recipient, the process comprising the steps of:

i) obtaining serum from a subject after liver transplantation at a time post operative when the serum contains a protein not normally present in serum, which protein is selected from a protein having a molecular weight of about 10 kD, about 40 kD or about 87 kD, or is a homologue of a 10 kD, 40 kD or 87 kD protein found in serum of a post liver transplantation rat;

ii) subjecting the serum from step (i) to at least one protein separative technique; and iii) isolating the 10 kD, 40 kD or 87 kD protein or homologue from the separated proteins.

In still another aspect, the invention provides a method of suppressing allograft rejection in a mammalian recipient, the method comprising administering to the recipient an immunosuppressive protein or fragment or chemical derivative thereof, or a pharmaceutical composition comprising the protein or fragment or derivative thereof, which protein is found in serum of a post liver transplantation subject and has a molecular weight selected from a molecular weight of about 10 kD, about 40 kD or about 87 kD, or is a homologue of a 10 kD, 40 kD or 87 kD protein found in serum of a post liver transplantation rat.

BEST MODE AND OTHER MODES FOR CARRYING OUT THE INVENTION

Figure 1:
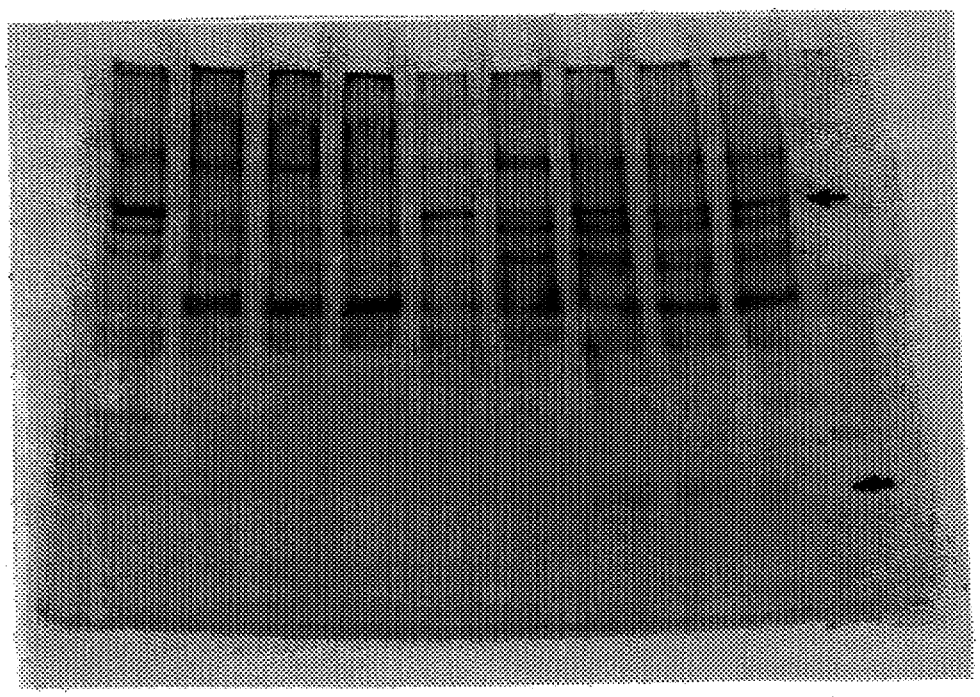
FIG. 1 depicts an analysis of serum samples taken from rats after orthotopic liver transplantation (OLT) and orthotopic liver retransplantation (re-OLT). The following samples were analysed: Lane A, PVG normal serum; Lanes B to D, OLT serum 21 days post transplantation; Lane E, re-OLT serum 1 day post transplantation; Lane F, re-OLT serum 7 days post transplantation; Lanes G to I, re-OLT serum 21 days post transplantation.

The listed abbreviations are used throughout the following description and claims:

| | |
|---|---|
| HHT | heterotopic heart transplantation |
| MHC | major histocompatability complex |
| MLR | mixed lymphocyte reaction |
| OLT | orthotopic liver transplantation |
| PAGE | polyacrylamide gel electrophoresis |
| re-OLT | orthotopic liver retransplantation |

The one-letter code for amino acids used conforms to the IUPAC-IUB standard described in *The Biochemical Journal* 219, 345–373 (1984).

Since the early days of clinical and experimental liver transplantation, it has been common knowledge that liver transplantation is unique compared to that of other organs. It was reported in the 1960's that liver grafts in pigs are not rejected and induce tolerance without immunosuppression. However, there were many disagreements regarding the significance of this finding as pigs are out-bred and therefore the results of the experiments were not conclusive.

Since 1977, the present inventors and collaborators have been investigating the phenomenon of non-rejection of liver using rats, and were the first in the world to develop techniques for orthotopic liver transplantation in the rat (which is now used as a standard model world wide). In certain combinations of donor and recipient rat strains, such as DA (MHC haplotype: RT1$^a$) into PVG (RT1$^c$), liver grafts are accepted without using any immunosuppressive drug. A state of systemic unresponsiveness is induced in which grafts of other organs such as skin, heart, kidney, pancreas or small bowel of the same donor type are accepted permanently. All of these "other organs" are normally rejected if no immunosuppressive drugs are used. Third party (WAG) heart grafts were rejected with only slight increase in survival time (see Table 1 of N Kamada and D G D Wright *Transplantation* 38, 217–221 [1984]).

In the same combination, PVG recipients, which had been sensitised by DA skin graft, failed to reject DA liver with grafts second-set kinetics. The liver graft not only failed to reject, but converted the state of heightened reactivity to donor graft characteristic of immune recipients into one of non-reactivity characteristic of tolerant animals.

Such immunosuppressive effects were transferable using serum from liver grafted rats (OLT serum). DA heart grafts, implanted into PVG recipients which were injected intravenously with 1 ml of serum from liver grafted rats at the same time as heart grafting, survived indefinitely. Third party (WAG) heart grafts were not enhanced: that is, the serum effect was strain-specific (see Table 2 of A Yamaguchi and N Kamada *Immunology* 72, 79 [1991]).

The present inventor has surprisingly found that compounds are present in serum of post liver transplantation subjects which suppress allograft rejection.

Identification of Immunosuppressive Compounds

The novel compounds having activity as suppressors of allograft rejection can be identified by analysis of serum samples taken from subjects following liver transplantation. Advantageously, the analysis is carried out using serum from orthotopic liver transplanation (OLT) or orthotopic liver retransplantation (re-OLT) subjects. Known methods of biochemical analysis can be used. Preferably, a method which analyses molecular weights of proteins is employed. Typically, the molecular weight analysis is carried out by SDS-polyacrylamide gel electrophoresis (SDS-PAGE). Protein bands in gels are typically detected by staining. Bands can also be detected immunologically using antibody to the protein of interest.

Serum samples are taken at various times after transplantation. Typically, samples are taken over a period of 1 to about 100 days. Analysis of samples and comparison with samples from normal donor and recipient animals, or samples taken from the specific donor and recipient pre-transplantation, allows identification of proteins unique to post-transplantation serum.

Purification and Characterisation of the Immunosuppressive Compounds

The novel proteins having activity as suppressors of allograft rejection can be purified by known procedures for purification of proteins and a number of different procedures can be used in combination. Advantageously, a procedure which relies on molecular weight separation is employed. A suitable molecular weight separative procedure is native PAGE.

Larger scale purification of the proteins is advantageously by affinity chromatography. A preferred affinity receptor is an antibody to the proteins. The antibody can be a polyclonal antibody or a monoclonal antibody.

The purified proteins can be characterised by standard biochemical techniques which include amino acid sequencing, mass spectroscopy and isoelectricfocussing. Advantageously, the purified proteins can be used to prepare antibody to the protein. As the proteins are immunosuppressive proteins, fragments thereof are typically used as immunogens. The fragments can be produced by proteolytic or chemical degradation of the proteins or by chemical synthesis of a peptide. Advantageously, the fragment is coupled to a carrier protein for generating antibody.

In vitro and in vivo techniques can be used to establish the biological activity of the proteins. A preferred in vitro technique is mixed lymphocyte reaction (MLR). A typical in vivo technique is skin grafting.

A preferred in vivo model relies on heterotopic heart transplantation (HHT) in an experimental animal. In a fully allogeneic combination, the heterotopically transplanted heart will be rejected and stops beating (in the rat, this occurs after 7 to 9 days). Suppression of rejection in a HHT animal can be used to assess the efficacy, optimal dose and method of administration of the immunosuppressive compounds.

Another in vivo model relies on OLT. OLT is performed using an animal donor with the recipient strain being a known rejector. In this combination, the recipient will not survive (in rats, a LEW OLT recipient of a DA donor will die within 12 days from acute rejection). Again, suppression of rejection in an OLT animal can be used to assess the activity of the immunosuppressive compounds.

Therapeutic Use of the Novel Compounds

The novel protein compounds of the invention have the potential for use as suppressors of rejection of transplanted organs in a mammalian subject, including a human subject. The invention includes within its scope use of the proteins either alone or in combination with other immunosuppressive compounds. The invention also encompasses pharmaceutical compositions comprising the novel proteins together with a pharmaceutically acceptable carrier, diluent and/or adjuvant.

Fragments of the proteins which retain immunosuppressive activity, and chemically modified protein and fragments, are included within the scope of the invention.

The proteins or compositions comprising the proteins are typically administered by intravenous routes at 10 µg/kg/day.

So that the invention may be more fully understood, non-limiting examples follow.

EXAMPLE 1

Identification of Immunosuppressive Compounds in OLT and re-OLT Rat Serum

The OLT technique for rats is described in N Kamada and R Y Calne *Transplantation* 28, 47 (1979), the entire disclosure of which is incorporated herein by cross-reference. Briefly, a first anastomosis is carried out in which the donor suprahepatic vena cava (SVC) is anastomosed to the recipient SVC whereafter a second anastomosis is carried out in which the donor SVC is anastomosed to a section of the recipient's diaphragm. In re-OLT, a sygeneic liver is transplanted shortly after the subject received an allogeneic liver transplant.

The following rats, each 8 to 16 weeks of age, were used for OLT, re-OLT or HHT with surgery performed as described by N Kamada in "Experimental rat liver transplantation" (CRC Press 1988): DA (MHC haplotype, RT1$^a$); PVG (MHC haplotype, RT1$^c$); and Lewis (MHC haplotype, RT1$^l$), (Animal Resources Centre, Perth, Australia). OLT was performed in the combination DA into PVG without immunosuppressive drugs and in the combination of DA into Lewis using the immunosuppressive drag, cyclosporin A (Sandoz, Basle, Switzerland) at a concentration of 10 mg/kg per day. HHT was carried out in the combination of DA into PVG using cyclosporin as described previously. For re-OLT, PVG liver transplanted into a PVG rat 2 days after OLT in the combination DA into PVG.

Blood samples, 1 ml, were taken from OLT rats (DA-PVG) at various times up to 107 days. Serum was separated from blood by centrifugation at 3,000g and stored at –20° C. until use. Serum samples were diluted 1:20 in doubled deionized water as was normal serum from PVG and DA rats. In re-OLT operations, blood samples (DA-PVG/PVG-PVG) taken at 1, 3, 7, 10 and 21 days were treated as outlined above. Samples from HHT rats (DA-PVG+Cys-A) were taken at the same time periods as OLT samples and treated in the same manner as was blood from PVG rats which had clamp and de-clamping performed. Five µl portions of these diluted serum samples were then added to Laemmli sample buffer (Laemmli *Nature* 227, 680 [1970]) and separated on 4–20% gradient SDS-PAGE gels and stained with Coomassie R-250 (Bio-Rad, Richmond, Calif., USA). Prestained low molecular weight standards (Bio-Rad) were also run to estimate the molecular weights of proteins of interest.

From the gel analysis presented in FIG. 1, it can be seen that a 10 kD protein and an 87 kD protein are present in rat serum shortly after replacement with the syngeneic PVG liver. The position of the 87 kD band is indicated by the upper arrow in FIG. 1 while the 10 kD band is indicated by the lower arrow.

The 10 kD protein is not present in normal donor DA serum or normal recipient PVG serum. The protein appears at a much lower concentration in OLT serum 21 days post transplantation. The protein was also detected in OLT serum 30 to 60 days post transplantation (data not shown).

The 87 kD protein is not present in normal donor DA serum or normal recipient PVG serum. The protein was not detected in OLT serum.

Figure 2:
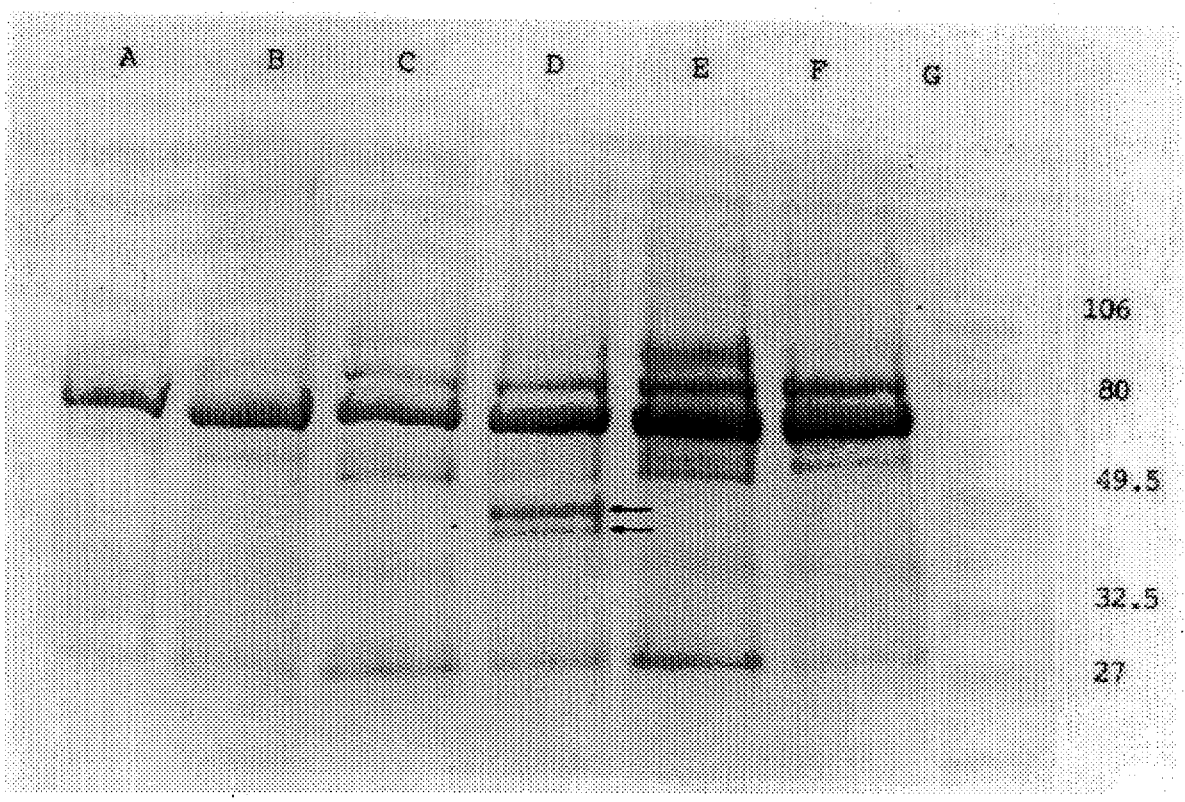
FIG. 2 depicts an analysis of serum samples taken from rats after orthotopic liver transplantation (OLT). The following samples were analysed: Lane A, DA normal serum; Lane B, PVG normal serum; Lane C, OLT serum 30 days post transplanation; Lane D, OLT serum 63 days post transplantation; Lane E, OLT serum 107 days post transplantation; and Lane F, HHT serum 63 days post transplantation.

The data of FIG. 2 show that a 40 kD protein and a 37 kD protein are present in large concentrations in diluted serum at 60 days post OLT. These proteins could be detected as early as 40 days post OLT but were undetectable at 107 days after OLT. The positions of the 40 kD and 37 kD protein bands in FIG. 2 are indicated by arrows.

The proteins could not be seen in either normal PVG or DA serum or in rats which had undergone HHT at 60 days post OLT (FIG. 2). The proteins were also not detectable in OLT serum at the same time from DA into Lewis combinations using the immunosuppressive drug cyclosporin or in serum from PVG rats which had OLT clamping but no liver transplant (data not shown). Although the proteins have identical N-termini, MLR assays demonstrated that the 37 kD protein is not immunosuppressive (data not presented).

EXAMPLE 2

Purification of the Proteins and Partial Sequence Determinations

Gels (native PAGE) of 4–20% were used to separate a number of portions of serum containing the three proteins of interest. One lane of each of the gels was stained to identify the position of a particular protein of interest, corresponding bands excised from the acrylamide matrix and protein electroeluted using a volatile ammonium bicarbonate buffer. Protein was HPLC purified to remove any contaminating material. The HPLC purified material was then lyopholyized in a Speed Vac Concentrator (Savant Instruments) and resuspended in either HPLC grade double deionized water or tissue culture medium. Tissue culture medium samples were subjected to further dialysis against RPMI. Additionally, rat albumin was purified in a similar fashion to be used as a control in in vitro MLR.

One ml of undiluted 21-day post re-OLT serum yielded 0.005 mg of purified 10 kD protein, 1 ml of undiluted 60 day post OLT serum yielded 0.12 mg of purified 40 kD protein, and 1 ml of undiluted 21-day post re-OLT serum yielded 0.03 mg of purified 87 kD protein.

For sequence determination, HPLC purified proteins were separated on TRIS-tricine gels and electrophoretically transferred to PVDF membrane using methods described in "Protein Blotting" Bulletin No. 1721, Bio Rad Corporation (1992) and "Proteins—Tips and Technologies", Promega Corporation (1993). Sequencing was carried out on an Applied Biosystems 473 Protein Sequenater using Edman chemistry.

The sequence over the first eleven to fifteen residues at the amino terminus of each protein was determined to be as follows:

| | |
|---|---|
| 10 kD | V H G A D A E T A I V N G X I |
| 40 kD | X S L A A T H M H G N |
| 87 kD | X E D I N F Q A F V E P H V |

The 10 kD, 40 kD and 87 kD proteins were designated "KX-4", "KX-5" and "KX-2" respectively.

EXAMPLE 3

Production of Polyclonal Antibody to Immunosuppressive Proteins

Twenty mg of peptide was synthesised based on each of the KX-4, KX-5 and KX-2 N-terminal sequences. Five mg of the peptide was conjugated to diphtheria toxoid (DT) and a further 5 mg conjugated to bovine serum albumin (BSA). Rabbits were inoculated with a 100–200 µg dose of DT-peptide in Freund's complete adjuvant (FCA) then boosted every two weeks for a total of six weeks with the same dosage in Freund's incomplete adjuvant (IFA). The antibody titre was subsequently measured by ELISA.

EXAMPLE 4

Immunosuppressive Activity of KX-4

The MLR assay was conducted in accordance with established procedures. Splenic lymphocytes from normal PVG and X-ray irradiated (2,000 R) DA, LEW or BN cells were used as responders and stimulators, respectively. Equal numbers ($5\times10^5$ cells each) were cultured in 200 µl total volumes in 96-well round-bottomed microculture plates (Corning, New York, N.Y.) for 3 days. Twenty hours before harvest, 0.5 µCi of [$^3$H]-thymidine was added to the culture. The culture medium consisted of RPMI-1640 (Gibco, Grand Island) containing 100 units/ml benzylpenicillin, 10 µg/ml streptomycin, 10 mM N-2-hydroxymethylpiperanzine-N'-2-ethanesulfonic acid, 50 µM sodium pyruvate (Gibco), 25 µM 2-mercaptoethanol (Gibco) and 10% foetal calf serum. Purified proteins in various concentrations were added to MLR wells. Normal PVG rat albumin was used in controls. The incorporated radioactivity was counted in a scintillation counter (1295-004 Beta plate 96 well harvester, Wallac). The incorporation of [$^3$H]-thymidine was determined and percentage inhibition was calculated as [1-{(c.p.m. of culture with added graft serum or purified proteins—c.p.m. of culture with responder cells only)/(c.p.m. of culture with added normal serum or rat albumin—c.p.m. of culture with responder cells only)}]×100(%).

TABLE I

MLR Results for KX-4

| Stimulator Cells | Responder Cells | Protein (amount) | $^3$H-uptake Exp. 1 | Exp. 2 |
|---|---|---|---|---|
| DA | PVG | KX-5 (10 µg) | 42.2 | |
| DA | PVG | KX-4 (5 µg) | 52.9 | 109.8 |
| DA | PVG | KX-4 (2.5 µg) | NT | 626.2 |
| DA | PVG | KX-4 (1 µg) | 10,836.8 | 10,625.3 |
| DA | PVG | KX-4 (0.5 µg) | 7,368.6 | 6,956.6 |
| DA | PVG | KX-4 (0.1 µg) | NT | 20,076.1 |
| DA | PVG | Albumin (10 µg) | 33,445.3 | NT |
| DA | PVG | Albumin (5 µg) | 35,181.3 | 30,971.7 |
| DA | PVG | Albumin (1 µg) | 30,670.3 | 31,552.4 |
| DA | PVG | Albumin (0.5 µg) | 29,059.5 | 37,564.1 |
| DA | PVG | Albumin (0.1 µg) | | 31,741.8 |
| LEW | PVG | KX-4 (10 µg) | 94.2 | |
| LEW | PVG | KX-4 (5 µg) | 86.4 | 74.4 |
| LEW | PVG | KX-4 (2.5 µg) | | 163.3 |
| LEW | PVG | KX-4 (1 µg) | 2,297.6 | 6,454.0 |
| LEW | PVG | KX-4 (0.5 µg) | 1,747.8 | 1,045.7 |
| LEW | PVG | KX-4 (0.1 µg) | | 8,773.3 |
| DA | PVG | — | 43,051.7 | 28,672.8 |
| LEW | PVG | — | 16,146.3 | 6,511.2 |
| — | PVG | — | 3,408.1 | 2,329.3 |
| DA | — | — | 212.4 | 55.6 |
| LEW | — | — | 115.5 | 49.6 |

It can be seen from the data of Table I that the KX-4 protein has a strong immunosuppressive effect: 0.5 µg in each well showed a 62% inhibition rate. The protein is donor specific at low concentration but becomes non-specific at higher concentrations.

EXAMPLE 5

Immunosuppressive Activities of KX-5 and KX-2

The immunosuppressive activities of KX-5 and KX-2 were tested as detailed above for KX-4 in Example 4. The results for KX-5 are presented below in Tables II and III and the KX-2 results in Table IV.

TABLE II

MLR Results for KX-5

| Stimulator Cells | Responder Cells | Protein (amount) | $^3$H-uptake Exp. 1 | Exp. 2 | Exp. 3 |
|---|---|---|---|---|---|
| DA | PVG | KX-5 (0.1 µg) | | | 20,560.1 |
| DA | PVG | KX-5 (0.5 µg) | | 4,081.9 | 3,315.0 |
| DA | PVG | KX-5 (1 µg) | 1,601.0 | 8,875.4 | 6,681.9 |
| DA | PVG | KX-5 (5 µg) | 2,126.8 | 3,699.3 | 4,561.4 |
| DA | PVG | KX-5 (10 µg) | 1,425.4 | 2,332.2 | |
| DA | PVG | Albumin (0.1 µg) | | | 31,741.8 |
| DA | PVG | Albumin (0.5 µg) | | 29,059.5 | 37,564.1 |
| DA | PVG | Albumin (1 µg) | 7,238.0 | 30,670.3 | 31,552.4 |
| DA | PVG | Albumin (5 µg) | 7,421.5 | 35,181.3 | 30,971.7 |
| DA | PVG | Albumin (10 µg) | 7,930.4 | 33,445.3 | |
| LEW | PVG | KX-5 (0.1 µg) | | | 3,782.9 |
| LEW | PVG | KX-5 (0.5 µg) | | 18,116.1 | 665.9 |
| LEW | PVG | KX-5 (1 µg) | 1,273.4 | 753.0 | 385.7 |
| LEW | PVG | KX-5 (5 µg) | 943.6 | 403.7 | 359.6 |
| LEW | PVG | KX-5 (10 µg) | 1,052.3 | 268.1 | |
| PA | PVG | — | 6,991.4 | 43,051.7 | 26,672.8 |
| LEW | PVG | — | 6,341.9 | 16,146.3 | 6,511.2 |
| — | PVG | — | 3,915.8 | 3,408.1 | 2,329.3 |

TABLE III

MLR Results for KX-5

| Stimulator Cells | Responder Cells | Protein | Amount | $^3$H-up take |
|---|---|---|---|---|
| DA | PVG | KX-5 | 0.1 µg | 24,478 ± 644 |
| | | | 0.5 µg | 2,737 ± 268 |
| | | | 1.0 µg | 3,098 ± 649 |
| | | | 5.0 µg | 2,978 ± 523 |
| DA | PVG | Albumin | 0.1 µg | 14,918 ± 3,015 |
| | | | 0.5 µg | 15,501 ± 3,044 |
| | | | 1.0 µg | 15,823 ± 5,473 |
| | | | 5.0 µg | 16,539 ± 1,814 |
| BN | PVG | KX-5 | 0.1 µg | 20,287 ± 1,850 |
| | | | 0.5 µg | 6,185 ± 182 |
| | | | 1.0 µg | 8,165 ± 1,963 |
| | | | 5.0 µg | 12,933 ± 1,204 |
| PVG | DA | KX-5 | 0.1 µg | 10,874 ± 2,954 |
| | | | 0.5 µg | 2,940 ± 700 |
| | | | 1.0 µg | 2,036 ± 378 |
| | | | 5.0 µg | 960 ± 101 |
| DA | PVG | — | | 16,867 ± 2,883 |
| BN | PVG | — | | 21,478 ± 3,099 |
| PVG | DA | — | | 16,236 ± 1,923 |
| — | PVG | — | | 2,050 ± 118 |
| — | DA | — | | 5,623 ± 345 |

It can be seen from the data of Tables II and III that the KX-5 immunosuppressive activity which is non-donor specific but is dose dependent.

TABLE IV

MLR Results for KX-2

| Stimulator Cells | Responder Cells | Protein (amount) | $^3$H-uptake Exp. 1 | Exp. 2 |
|---|---|---|---|---|
| DA | PVG | KX-2 (1 µg) | 98,064 ± 2,659 | 2,833 ± 349 |
|  |  | KX-2 (5 µg) | 5,532 ± 165 | NT |
|  |  | KX-2 (10 µg) | 3,454 ± 273 | NT |
|  |  | Albumin (1 µg) | 101,067 ± 4,827 | 15,823 ± 5,473 |
|  |  | Albumin (5 µg) | 106,649 ± 8,206 | 16,539 ± 1,814 |
|  |  | Albumin (10 µg) | 108,835 ± 3,805 | NT |
| BN | PVG | KX-2 (1 µg) | 76,254 ± 1,019 | 23,925 ± 7,598 |
|  |  | KX-2 (5 µg) | 5,632 ± 1,290 | NT |
|  |  | KX-2 (10 µg) | NT | NT |
| PVG | DA | KX-2 (1 µg) | 53,929 ± 2,414 | 12,953 ± 3,375 |
|  |  | KX-2 (5 µg) | 2,757 ± 2,757 | NT |
|  |  | KX-2 (10 µg) | 1,035 ± 316 | NT |
| DA | PVG | — | 118,718 ± 4,060 | 16,867 ± 2,883 |
| BN | PVG | — | 121,771 ± 5,198 | 21,478 ± 3,099 |
| PVG | DA | — | 56,327 ± 1,635 | 16,236 ± 1,926 |
| — | PVG | — | 29,795 ± 1,273 | 2,050 ± 118 |
| — | DA | — | 31,432 ± 2,597 | 5,623 ± 345 |

It can be seen from the data of Table IV that the KX-2 protein has immunosuppressive activity which is dose dependent but non-donor specific.

EXAMPLE 6

In vivo Testing of KX-5

The effect of KX-5 as an immunosuppressent was further tested in vivo using an HHT model. Hearts were obtained from DA or BN strain rats (donors) and implanted into the necks of PVG strain recipients. The transplantation technique employed is described in *Experimental Rat Liver Transplantation* (N. Kamada, ed., *CRC Press* 1988), the entire content of which is incorporated herein by cross-reference.

Experimental animals were divided into control and test groups. The control group received no treatment or 1 ml of intralipid intramuscularly. The test group received a single 300 µg dose of purified KX-5 (see Example 2) administered intramuscularly immediately after heart grafting while animals were under ether anaesthesia.

The results of the in vivo experiment are presented below in Table V.

TABLE V

Survival of heart allografts in PVG recipients

| Group | Strain of heart donor | Treatment of receipient | Heart graft survival (individual rats, days) | P value |
|---|---|---|---|---|
| 1 (control) | (A) DA | none | 7, 7, 8, 8, 8, 8, 8, 8, 8, 9, 9, 9 |  |
|  | (B) BN | none | 7, 7, 8, 8, 8, 8, 9, 9, 9, 9 |  |
|  | (C) DA | 1 ml of intralipid | 7, 7, 8, 8, 9, 9 | NS |
|  | (D) BN | (as above) | 7, 8, 8, 8, 9, 9 | NS |
| 2 (test) | (A) DA | KX-5, 300 µg | >100, >100, >100 | P < 0.001 |
|  | (B) BN | KX-5, 300 µg | 32, 65, >100 | P < 0.001 |

The results for the Group 2 animals clearly indicate that the KX-5 protein has a pronounced effect on the survival of heart grafts.

I claim:

1. A protein which suppresses allograft rejection in rats, which protein is found in serum of a post liver transplantation rat but is not normally found in serum and is a protein having a molecular weight selected from the group consisting of about 10 kD, about 40 kD and about 87 kD, as determined by SDS-PAGE under reducing conditions.

2. A protein according to claim 1, wherein said protein is found in serum of a post orthotopic liver transplantation or post orthotopic liver retransplantation rat.

3. A protein according to claim 1, wherein said protein has a molecular weight of about 10 kD and an N-terminal amino acid sequence corresponding to SEQ ID NO: 1.

4. A protein according to claim 1, wherein said protein has a molecular weight of about 40 kD and an N-terminal amino acid sequence corresponding to SEQ ID NO: 2.

5. A protein according to claim 1, wherein said protein has a molecular weight of about 87 kD and an N-terminal amino acid sequence corresponding to SEQ ID NO: 3.

6. A process for preparing a protein which suppresses allograft rejection in an individual of a mammalian species, the process comprising the steps of:
    i) obtaining serum from a representative of said species after liver transplantation at a time post operative when the serum contains a protein not normally present in serum, which protein is a protein having a molecular weight selected from the group consisting of about 10 kD, about 40 kD and about 87 kD, as determined by SDS-PAGE under reducing conditions;
    ii) subjecting the serum from step (i) to at least one protein separative technique; and iii) isolating said protein having said molecular weight selected from the group consisting of 10 kD, 40 kD and 87 kD from said separated proteins.

7. The method according to claim 6, wherein said at least one protein separative technique is selected from the group consisting of native polyacrylamide gel electrophoresis, affinity chromatography and high performance liquid chromatography.

8. A pharmaceutical composition comprising at least one of a pharmaceutically acceptable carrier diluent and adjuvant together with at least one immunosuppressive protein, which protein is found in serum of a post liver transplantation rat but is not normally found in serum and is a protein having a molecular weight selected from the group consisting of about 10 kD, about 40 kD and about 87 kD, as determined by SDS-PAGE under reducing conditions.

9. The composition according to claim 8, wherein said protein has a molecular weight of about 10 kD, and has an N-terminal amino acid sequence corresponding to SEQ ID NO: 1.

10. The composition according to claim 8, wherein said protein has a molecular weight of about 40 kD, and has an N-terminal amino acid sequence corresponding to SEQ ID NO: 2.

11. The composition according to claim 8, wherein said protein has a molecular weight of about 87 kD, and has an N-terminal amino acid sequence corresponding to SEQ ID NO: 3.

12. A method of suppressing allograft rejection in an individual of a mammalian species, the method comprising administering to said individual an immunosuppressive protein found in serum of a post liver transplantation representative of said species but is not normally found in serum, which protein is a protein having a molecular weight selected from the group consisting of about 10 kD, about 40 kD and about 87 kD, as determined by SDS-PAGE under reducing conditions.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Rattus rattus
    ( B ) STRAIN: PVG ( x i ) SEQUENCE DESCRIPTION: SEQ ID NO: 1:

```
Val His Gly Ala Asp Ala Glu Thr Ala Ile Val Asn Gly Xaa Ile
1               5                   10                  15
```

( 2 ) INFORMATION FOR SEQ ID NO: 2:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus rattus
        ( B ) STRAIN: PVG ( x i ) SEQUENCE DESCRIPTION: SEQ ID NO: 2:

```
Xaa Ser Leu Ala Ala Thr His Met His Gly Asn
1               5                   10
```

( 2 ) INFORMATION FOR SEQ ID NO: 3:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus rattus
        ( B ) STRAIN: PVG ( x i ) SEQUENCE DESCRIPTION: SEQ ID NO: 3:

```
Xaa Glu Asp Ile Asn Phe Gln Ala Phe Val Glu Pro His Val
1               5                   10
```